(12) United States Patent
Endo

(10) Patent No.: US 8,562,135 B2
(45) Date of Patent: Oct. 22, 2013

(54) OPHTHALMIC APPARATUS

(75) Inventor: Masakazu Endo, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 13/222,273

(22) Filed: Aug. 31, 2011

(65) Prior Publication Data
US 2013/0050643 A1    Feb. 28, 2013

(51) Int. Cl.
*A61B 3/10* (2006.01)
*A61B 3/14* (2006.01)

(52) U.S. Cl.
USPC .......................................... 351/206; 351/205

(58) Field of Classification Search
USPC .......................................... 351/205, 206, 221
See application file for complete search history.

(56) References Cited

U.S. PATENT DOCUMENTS

| | | | |
|---|---|---|---|
| 6,074,063 A * | 6/2000 | Hanaki | 351/206 |
| 7,506,980 B2 | 3/2009 | Fujieda | |
| 2003/0107708 A1* | 6/2003 | Isogai | 351/200 |
| 2012/0249955 A1* | 10/2012 | Sarver et al. | 351/206 |

FOREIGN PATENT DOCUMENTS

| | | |
|---|---|---|
| JP | 2003-169778 A | 6/2003 |
| JP | 2005-160694 A | 6/2005 |

* cited by examiner

*Primary Examiner* — Mahidere Sahle
(74) *Attorney, Agent, or Firm* — Lowe Hauptman & Ham, LLP

(57) ABSTRACT

An ophthalmic apparatus includes: a light projecting optical system for projecting measurement light on a cornea of an examinee's eye; a first imaging optical system for imaging a cornea reflection image obtained by reflection of the measurement light at the cornea; a computing unit for obtaining a direction of a corneal astigmatic axis based on the cornea reflection image; an illuminating optical system for projecting illumination light toward a fundus of the examinee's eye; a second imaging optical system for imaging a retro-illumination image in a pupil of the examinee's eye obtained by reflection of the illumination light at the fundus; an image processing unit for combining a first target representing the direction of the astigmatic axis with the retro-illumination image; and an output unit for outputting the retro-illumination image with which the first target has been combined.

12 Claims, 3 Drawing Sheets

OPHTHALMIC APPARATUS

CROSS-REFERENCE TO RELATED APPLICATION

This application is based on Japanese Patent Application No. 2010-057466 filed with the Japan Patent Office on Mar. 15, 2010, the entire content of which is hereby incorporated by reference.

BACKGROUND

1. Technical Field

The present disclosure relates to an ophthalmic apparatus for obtaining a retro-illumination image of an examinee's eye and a method of obtaining a retro-illumination image of an examinee's eye by use of the ophthalmic apparatus.

2. Related Art

In recent years, as one of intraocular lenses, a TORIC-Intraocular lens for astigmatism correction has been developed. In a case of prescribing such a TORIC-Intraocular lens, a corneal curvature and a corneal astigmatic axis are calculated by a keratometer (for example, refer to JP-A-2003-169778). Also, an ocular axial length is calculated by an ocular axial length measurement apparatus. Based on these results, a TORIC-Intraocular lens to be inserted is determined.

Subsequently, an operator puts a first mark in a direction of a horizontal axis of an examinee's eye by use of a dedicated member. The operator also puts a second mark at a position corresponding to an astigmatic axis (strong principal meridian direction) of the examinee's eye with reference to the first mark. The operator inserts the intraocular lens into the eye such that the second mark and an astigmatic axis of the TORIC-Intraocular lens may correspond to each other.

SUMMARY

An ophthalmic apparatus includes: a light projecting optical system for projecting measurement light on a cornea of an examinee's eye; a first imaging optical system for imaging a cornea reflection image obtained by reflection of the measurement light at the cornea; a computing unit for obtaining a direction of a corneal astigmatic axis based on the cornea reflection image; an illuminating optical system for projecting illumination light toward a fundus of the examinee's eye; a second imaging optical system for imaging a retro-illumination image in a pupil of the examinee's eye obtained by reflection of the illumination light at the fundus; an image processing unit for combining a first target representing the direction of the astigmatic axis with the retro-illumination image; and an output unit for outputting the retro-illumination image with which the first target has been combined.

DESCRIPTION OF EMBODIMENTS

Figure 1:
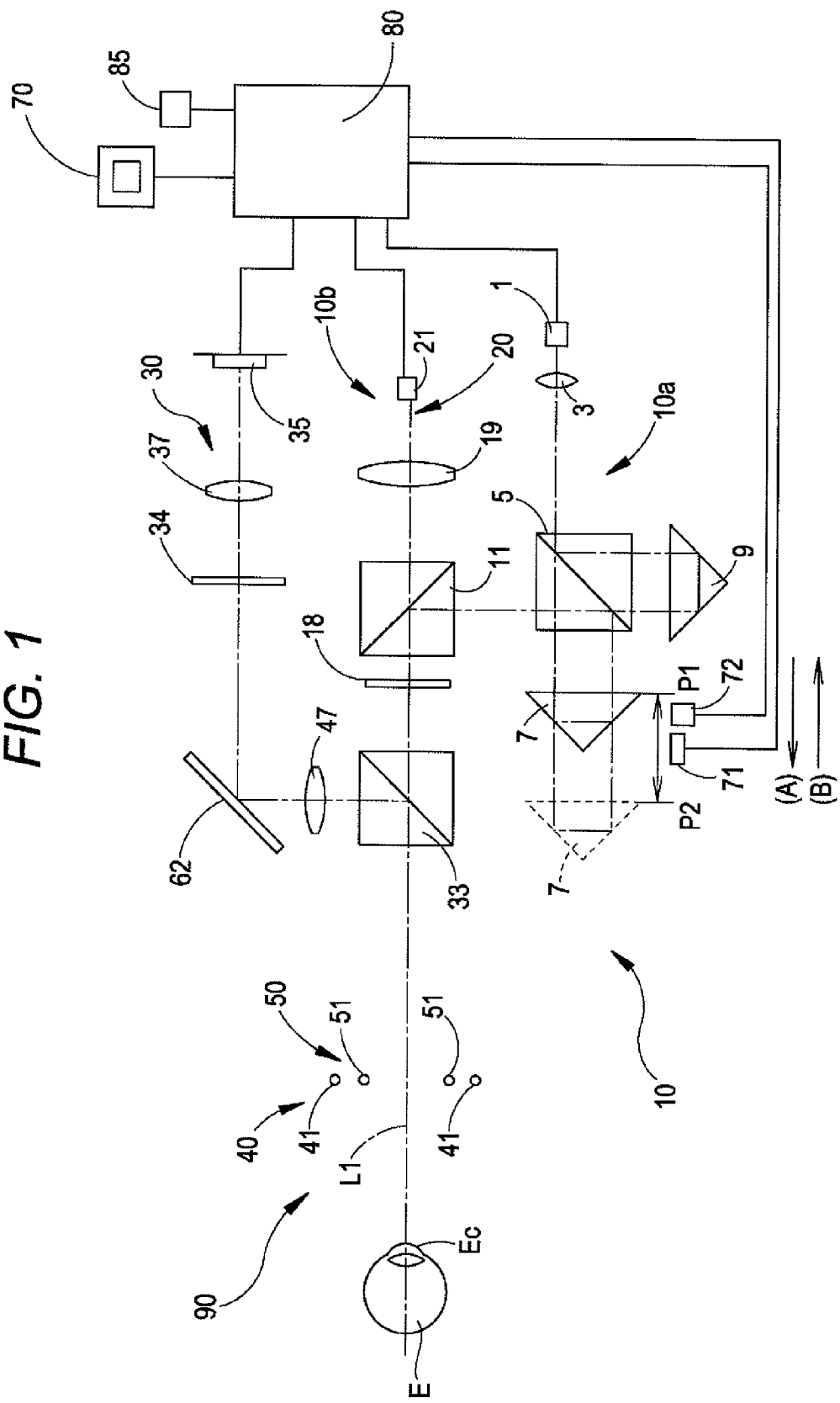
FIG. 1 is a schematic configuration diagram of an optical system and a control system of an ophthalmic apparatus.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

When the TORIC-Intraocular lens is inserted in the eye in a state where the direction of the astigmatic axis of the examinee's eye and the direction of the astigmatic axis of the TORIC-Intraocular lens are misaligned, a sufficient correction result may not be obtained in some cases. There exist a number of factors for causing such misalignment to occur. Examples of the factor include inability to put a mark at the astigmatic axis because the patient's posture changes at the time of measuring the corneal shape and at the time of putting the mark and occurrence of the operator's hand tremor at the time of inserting the intraocular lens. Also, there is a case where axial misalignment occurs until the intraocular lens becomes stable in the eye after the operation. Heretofore, there is no apparatus that is capable of checking the amount (extent) of the above axial misalignment after the operation.

An ophthalmic apparatus (present apparatus) according to an embodiment is described below with reference to the drawings. FIG. 1 is a schematic configuration diagram of an optical system and a control system of the present apparatus.

The optical system of the present apparatus is broadly classified into an ocular axial length measuring optical system (hereinafter, measuring optical system) 10, a projecting optical system 40, an alignment projecting optical system 50, and an anterior segment front imaging optical system 30 (hereinafter, imaging optical system). Also, a light projecting system of the measuring optical system 10 and the imaging optical system 30 are also used as an optical system for imaging a retro-illumination image by projecting illumination light on a fundus and receiving the reflection light on an imaging device 35.

These optical systems are built in a casing that is not illustrated. The casing is driven by a well-known alignment shifting mechanism via an operation member (for example, a joystick). Thus, the casing is moved three-dimensionally with respect to the examinee's eye.

The projecting optical system (light projecting optical system) 40 has a ring-shaped light source 41 disposed with a measurement optical axis L1 as the center. The projecting optical system 40 is used for measuring the corneal shape (including curvature and astigmatic axial angle) by projecting a ring target on the cornea of the examinee's eye. As the light source 41, for example, an LED generatable of infrared light or visible light is used.

The alignment projecting optical system 50 has a projection light source 51 that is generatable of infrared light and is disposed inside the light source 41. The light source 51 is used for projecting an alignment target on the cornea of the examinee's eye. The alignment target projected on the cornea is used for alignment of the present apparatus with the examinee's eye (for example, auto-alignment, alignment detection, and manual alignment). In the embodiment, the projecting optical system 50 is an optical system for projecting a ring target on the cornea of the examinee's eye. The ring target is also used as a Mayer ring. The light source 51 of the projecting optical system 50 is also used as an anterior segment light for illuminating the anterior segment with infrared light from a diagonal direction.

The imaging optical system (a first imaging optical system and a second imaging optical system) 30 is used for imaging an anterior segment front image of the examinee's eye. The imaging optical system 30 has a dichroic mirror 33, an objective lens 47, a mirror 62, a filter 34, an imaging lens 37, and a two-dimensional imaging device 35. The two-dimensional imaging device 35 is disposed at a position to be approximately conjugated with the anterior segment.

Anterior segment reflection light, which is obtained when light from the projecting optical system 40 and the projecting optical system 50 described above is reflected at the anterior segment, is formed into an image on the two-dimensional imaging device 35 via the dichroic mirror 33, the objective lens 47, the mirror 62, the filter 34, and the imaging lens 37.

The ocular axial length measuring optical system 10 projects measurement light onto the examinee's eye and detects interference light obtained by the interference of the reflection light from the examinee's eye. The ocular axial length measuring optical system 10 has a light projecting optical system 10a and a light receiving optical system 10b. The light projecting optical system (illuminating optical system) 10a includes a measurement light source 1, a collimator lens 3, a beam splitter 5, a first triangular prism (corner cube) 7, a second triangular prism 9, a polarizing beam splitter 11, and a quarter wavelength plate 18. The measurement light source 1 is a light source for emitting low coherent light (in the embodiment, the measurement light source 1 is also a fixation lamp). The collimator lens 3 makes a light flux emitted from the measurement light source 1 into a parallel light flux. The beam splitter 5 splits light emitted from the light source 1. The first triangular prism (corner cube) 7 is disposed in the transmission direction of the beam splitter 5. The second triangular prism 9 is disposed in the reflection direction of the beam splitter 5. Meanwhile, the measurement light source 1 is also used as a fixation lamp in the embodiment. However, a separate fixation lamp may be provided.

Light (linearly polarized light) emitted from the light source 1 is collimated by the collimator lens 3, and then split by the beam splitter 5 into a first measurement light beam and a second measurement light beam. The first measurement light beam is reflected by the triangular prism 7 and bent back. Meanwhile, the second measurement light beam is reflected by the triangular prism 9 and bent back. Subsequently, the first measurement light beam and the second measurement light beam are combined by the beam splitter 5. The combined light is reflected by the polarizing beam splitter 11, and then converted to circularly polarized light by the quarter wavelength plate 18. Then, at least the cornea and fundus of the examinee's eye are irradiated with the circularly polarized light via the dichroic mirror 33. At this time, when the measurement light flux including the circularly polarized light is reflected at the cornea and fundus of the examinee's eye, the phase of the light flux is displaced by ½ a wavelength.

The light receiving optical system 10b is disposed for receiving light (interference light) obtained by the interference of cornea reflection light, which is obtained when measurement light is reflected at the cornea, and fundus reflection light, which is obtained when measurement light is reflected at the fundus. The light receiving optical system 10b includes the dichroic mirror 33, the quarter wavelength plate 18, the polarizing beam splitter 11, a condenser lens 19, and a light receiving device 21.

The cornea reflection light and the fundus reflection light pass through the dichroic mirror 33, and then are converted to linearly polarized light by the quarter wavelength plate 18. Subsequently, both kinds of reflection light having passed through the polarizing beam splitter 11 are condensed by the condenser lens 19 and then received by the light receiving device 21.

The triangular prism 7 is used as an optical-path-length changing member for changing the optical path length. The triangular prism 7 is moved linearly relative to the beam splitter 5 along the optical axis direction by the driving of a driving part 71 (for example, a motor). The optical-path-length changing member may also be a triangular mirror. The position of the prism 7 during driving is detected by a position detecting sensor 72 (for example, a potentiometer or an encoder).

A configuration in which the cornea reflection light and the fundus reflection light are made to interfere has been described above. However, this configuration does not have to be provided. In other words, the present apparatus may be an ophthalmic apparatus (eye dimension measurement apparatus) including an optical interference optical system including a beam splitter (light splitting member) for splitting light emitted from a light source, a sample arm, a reference arm, and a light receiving device for receiving interference light. In this optical interference optical system, interference light obtained by the interference of measurement light with which the examinee's eye is irradiated via the sample arm and reference light from the reference arm is received by the light receiving device. In this case, the optical-path-length changing member is disposed on at least any of the sample arm and the reference arm.

In the above configuration, the optical path length of reference light is changed through linear movement of the prism 7. However, this configuration does not have to be provided. For example, the present apparatus may have a configuration in which the optical path length of reference light is changed by an optical delay mechanism via a rotating reflector (for example, refer to JP-A-2005-160694).

In the present apparatus, the measurement light source 1 of the ocular axial length measuring optical system 10 is also used as a light source for imaging a retro-illumination image. Light for imaging the retro-illumination image is projected on the fundus of the examinee's eye through a similar optical path to that of the light projecting optical system 10a. The inside of the pupil of the examinee's eye is then illuminated from the back by fundus reflection light, which is obtained when this light is reflected at the fundus. Light emitted from the pupil of the examinee's eye is imaged by the two-dimensional imaging device 35 through a similar path to that of the aforementioned anterior segment reflection light. In this manner, the retro-illumination image in the pupil of the examinee's eye is obtained.

Next, the control system is described. A control part (a computing unit and an image processing unit) 80 performs control of the entire apparatus and calculation of measurement results. The control part 80 is connected, for example, to the light source 1, the light source 51, the light source 41, the light receiving device 21, the imaging device 35, a monitor 70, and a memory 85.

The operation overview of the present apparatus is described. The memory 85 stores a cornea reflection image (refer to FIG. 2) and a retro-illumination image (refer to G in FIG. 3) obtained from image signals outputted from the imaging device 35. The control part 80 detects a direction of a corneal astigmatic axis by use of the cornea reflection image stored on the memory 85 (refer to FIG. 2).

Figure 5:
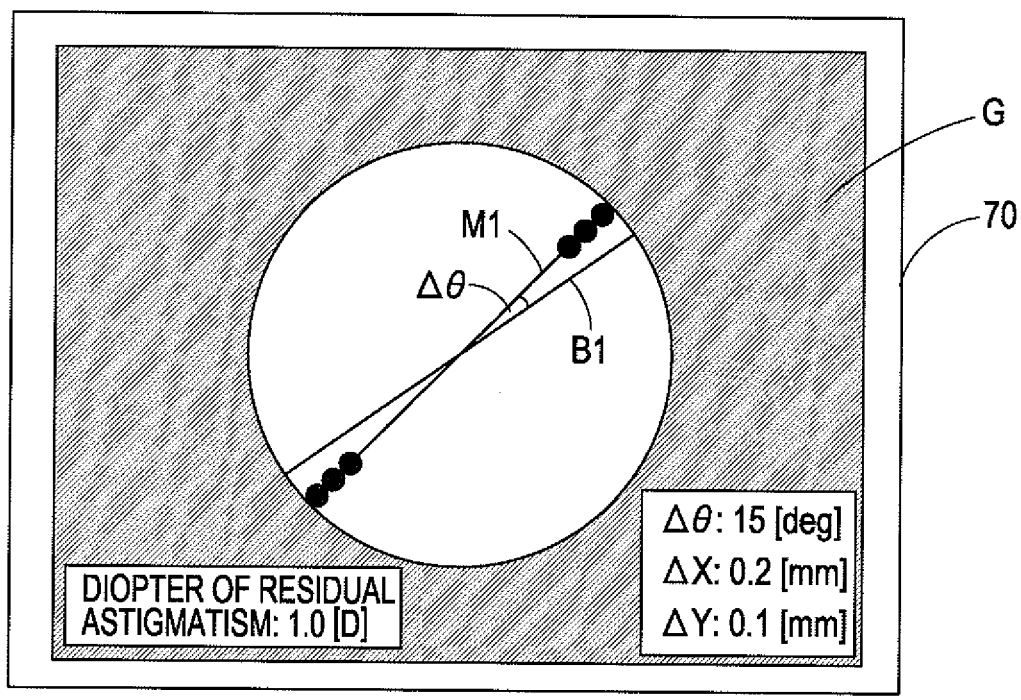
FIG. 5 depicts the retro-illumination image with which the luminance change portions have been combined.

The control part 80 executes processing of superimposing a corneal astigmatic axis target (refer to the line B1 in FIG. 5)

representing the direction of the corneal astigmatic axis onto the retro-illumination image (refer to G in FIG. 3) stored on the memory 85 by use of the detection result of the direction of the corneal astigmatic axis. The control part 80 then outputs the retro-illumination image on which the corneal astigmatic axis target has been superimposed (refer to FIG. 5).

In this case, the control part 80 detects lens astigmatic axis information of a TORIC-Intraocular lens (a direction of an astigmatic axis of the TORIC-Intraocular lens) based on the retro-illumination image stored on the memory 85. Alternatively, the lens astigmatic axis information is detected, for example, based on an astigmatic axis mark 91 formed (inscribed) on the intraocular lens in advance (refer to FIGS. 3 and 4).

Subsequently, the control part 80 displays a lens astigmatic axis target (refer to the line M1 in FIG. 5) representing the direction of the astigmatic axis of the TORIC-Intraocular lens based on the detected lens astigmatic axis information together with the corneal astigmatic axis target (refer to the line B1 in FIG. 5). In this case, the lens astigmatic axis target is displayed in a state of being superimposed, for example, on the retro-illumination image including the astigmatic axis mark. Alternatively, the lens astigmatic axis target may be displayed in a state of being superimposed on an anterior segment image. Also, the lens astigmatic axis target may be displayed at an end portion of the monitor.

Figure 3:
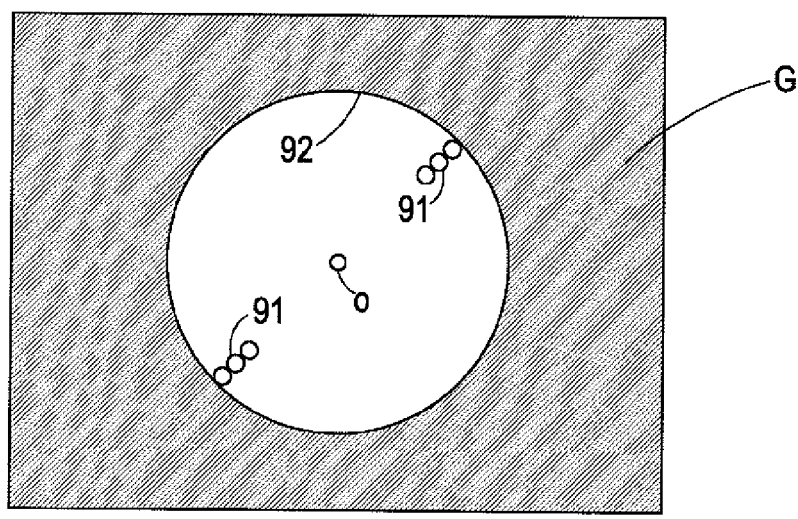
FIG. 3 depicts a screen displaying an imaged retro-illumination image.
Figure 4:
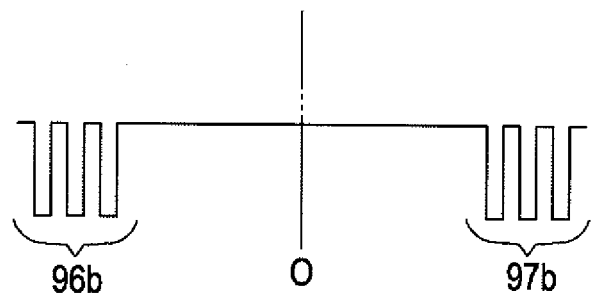
FIG. 4 depicts a detection result of luminance change portions corresponding to astigmatic axis marks by image processing for the retro-illumination image.

In the case of detecting the astigmatic axis mark 91, the control part 80, for example, detects a luminance change portion corresponding to the astigmatic axis mark 91 by image processing of the retro-illumination image stored on the memory 85 (refer to FIGS. 3 and 4). The control part 80 then derives the lens astigmatic axis target (refer to the line M1 in FIG. 5) based on the detected luminance change portion. The control part 80 then superimposes the lens astigmatic axis target onto the retro-illumination image.

The control part 80 also detects an axial misalignment amount, which is a misalignment amount between the direction of the corneal astigmatic axis and the direction of the lens astigmatic axis, and displays the detection result together with the retro-illumination image (refer to $\Delta\theta$ in FIG. 5). In detection of the axial misalignment amount, the control part 80 may detect the axial misalignment amount by deriving the angle (direction) of the lens astigmatic axis and the angle (direction) of the corneal astigmatic axis separately and comparing these angles with each other. Alternatively, the control part 80 may detect the misalignment amount (axial misalignment amount) between the direction of the corneal astigmatic axis and the direction of the lens astigmatic axis by image processing with reference to a certain center point.

Figure 2:
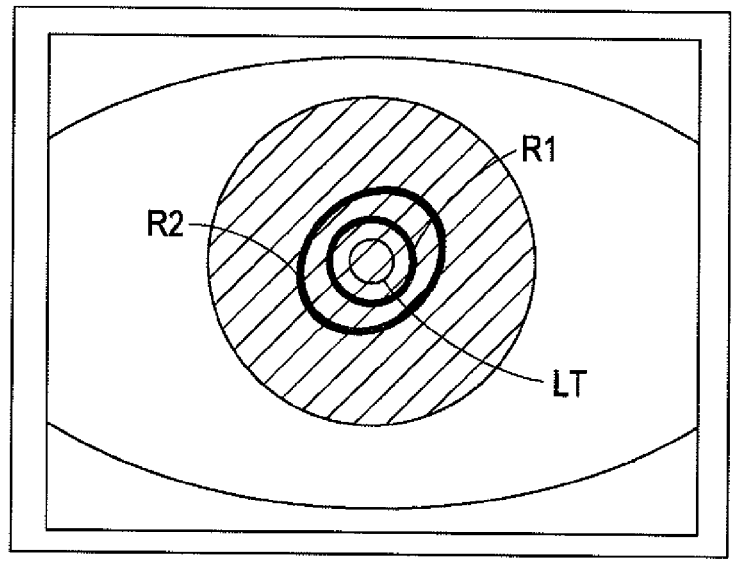
FIG. 2 depicts an anterior segment observation screen displaying an imaged anterior segment image.

Further, the control part 80 detects a corneal center position based on the cornea reflection image stored in the memory 85 (refer to FIG. 2). The control part 80 also detects an optical center position of the intraocular lens based on the retro-illumination image stored on the memory 85. The control part 80 then detects a misalignment amount between the corneal center position and the optical center position (refer to FIG. 3). The control part 80 then displays the detected misalignment amount together with the retro-illumination image.

Next, specific operation examples of the present apparatus are described in details. Driving modes of the present apparatus include a preoperative mode and a postoperative mode. The preoperative mode is a mode for measuring, for example, the corneal shape of the examinee's eye and deriving the dioptic power of the intraocular lens. The postoperative mode is a mode for checking the axial misalignment amount by checking an insertion position of the TORIC-Intraocular lens in the examinee's eye after the operation. In the postoperative mode in the embodiment, the control part 80 images the examinee's eye in which the TORIC-Intraocular lens has been inserted (TORIC-Intraocular lens insertion eye) and measures the misalignment amount (axial misalignment amount) between the direction of the corneal astigmatic axis and the direction of the intraocular lens astigmatic axis. Operations of the present apparatus in the postoperative mode in the embodiment are described below.

<Kerato Imaging>

When a not-shown switch for conducting switch to the postoperative mode is selected by the examiner, the control part 80 switches the mode of the present apparatus from the preoperative mode to the postoperative mode. Meanwhile, the examinee's eye may be in a state of pupil dilation by a dilating agent in the postoperative mode.

First, the corneal shape is measured. FIG. 2 depicts an anterior segment observation screen displaying an anterior segment image imaged by the imaging device 35. For alignment, the light source 51 and the light source 41 are illuminated. The examiner carries out alignment of the present apparatus in the up-down and right-left directions such that a reticle LT displayed electronically and a ring target R1 by the light source 51 may be concentric as depicted in FIG. 2. The examiner also carries out alignment of the present apparatus in the front-rear direction such that the ring target R1 may be in focus. On the outer side of the ring target R1, a ring target R2 by the light source 41 is displayed.

After the alignment of the present apparatus is carried out in the above manner, a predetermined trigger signal is generated. In response to this, the control part 80 images an anterior segment image. Subsequently, the control part 80 obtains an anterior segment image including the ring targets R1 and R2 as a still image based on an imaging signal outputted from the imaging device 35 for storage on the memory 85 (refer to FIG. 2).

The control part 80 then calculates the corneal shape of the examinee's eye (for example, cornea curvature in a strong principal meridian direction and a weak principal meridian direction, and corneal astigmatic axial angle) based on the ring target R2 on the anterior segment image stored on the memory 85 and stores the calculation result on the memory 85. In a corneal astigmatic eye, the image of the ring target R2 is in an oval shape. Accordingly, the control part 80 derives the corneal astigmatic axial angle by detecting its longer-diameter direction and shorter-diameter direction. Further, the control part 80 detects coordinates of a corneal center position of the examinee's eye based on the ring target R1 or the ring target R2 and stores the detection result on the memory 85.

<Retro-Illumination Image Imaging>

When imaging of the anterior segment image including the ring targets is finished, the control part 80 extinguishes the light source 51 and the light source 41 and illuminates the light source 1. The control part 80 causes the imaging device 35 to image a retro-illumination image based on the fundus reflection light, which is obtained when light of the light source 1 is reflected at the fundus. The control part 80 stores the imaged retro-illumination image on the memory 85 (refer to FIG. 3).

As depicted in FIG. 3, an iris portion of the examinee's eye dims the fundus reflection light. Accordingly, the iris portion is imaged by the imaging device 35 as a dark image (refer to a pupil area 92 in FIG. 3). The pupil area 92 represents a border position between the iris and the pupil.

The astigmatic axis mark representing the position of the astigmatic axis of the TORIC-Intraocular lens (hereinafter referred to as IOL as well) inside the pupil area 92 dims the fundus reflection light. Accordingly, the astigmatic axis mark is imaged by the imaging device 35 as a dark image (refer to the astigmatic axis mark 91 in FIG. 3). Also, the other area in the pupil passes the fundus reflection light and is thus imaged by the imaging device 35 as a bright image.

<Combination Processing of Corneal Shape Measurement Result and Retro-Illumination Image>

Subsequently, the control part 80 creates a combination image for checking the misalignment amount (axial misalignment amount) between the direction of the corneal astigmatic axis and the direction of the IOL astigmatic axis based on the angular data of the corneal astigmatic axis of the examinee's eye and the retro-illumination image that are stored on the memory 85.

FIG. 3 depicts the imaged retro-illumination image. The control part 80 first detects the edge of the pupil area 92 from the light quantity distribution of the retro-illumination image. Based on this detection result, the control part 80 then obtains a pupil shape and calculates a pupil center O.

Subsequently, the control part 80 measures the luminance of the edge of the pupil area 92 on the entire circumference along the circumferential direction of the edge centering on the pupil center O once per degree.

At a position in the IOL at which the astigmatic axis mark 91 is formed, a luminance change due to the astigmatic axis mark 91 occurs (refer to FIG. 4). On the other hand, at a position at which no astigmatic axis mark 91 is formed, almost no luminance change occurs. As depicted in FIG. 3, the astigmatic axis marks 91 are formed at two positions that are symmetric about the optical center of the IOL.

More specifically, two luminance change portions 96b and 97b corresponding to two positions at which the astigmatic axis marks 91 are formed are detected on the luminance distribution at the edge of the pupil area 92, as depicted in FIG. 4. That is, the control part 80 analyzes a measurement result of the luminance distribution at the edge of the pupil area 92. As a result, the control part 80 detects the luminance change portions 96b and 97b resulting from the astigmatic axis marks 91. Thus, the control part 80 can detect positions at which astigmatic axis marks 91 are formed.

FIG. 5 depicts a specific example of an image obtained by combining the measurement result of the corneal shape and the retro-illumination image. The combination is performed by image processing. The control part 80 derives coordinates of a position of a straight line connecting the detected positions at which the two astigmatic axis marks 91 are formed. The control part 80 combines this straight line with the retro-illumination image as the line M1. The line M1 acts as a target representing the astigmatic axis of the IOL.

The control part 80 also combines a straight line corresponding to the astigmatic axial angle calculated as above with the retro-illumination image as the line B1. The line B1 acts as a target representing the direction of the corneal astigmatic axis of the examinee's eye (corneal astigmatic axis target).

Herein, the control part 80 detects a center position between the two astigmatic axis marks 91. The control part 80 then displays the line B1 on the retro-illumination image on the monitor 70 such that the line B1 may pass on the center position. At this time, a center of the line B1 may correspond to the center position between the two astigmatic axis marks 91 to facilitate recognition of the angle between the line M1 and the line B1.

Further, the control part 80 detects a misalignment amount between the corneal center position detected as above and the center position between the two astigmatic axis marks 91. The control part 80 then displays the detection result on the monitor 70 together with the retro-illumination image. This is combined with the retro-illumination image, for example, as misalignment amounts in X and Y directions ($\Delta X$, $\Delta Y$) as illustrated in FIG. 5.

Further, the control part 80 calculates an angular difference $\Delta\theta$ between the astigmatic axial angle of the cornea and the astigmatic axial angle of the IOL based on the angle between the astigmatic axis of the IOL (line M1) and the astigmatic axis of the cornea of the examinee's eye (line B1). The control part 80 displays the calculation result together with the retro-illumination image. The angular difference $\Delta\theta$ combined with the retro-illumination image represents the misalignment amount (axial misalignment amount) between the direction of the corneal astigmatic axis and the direction of the IOL astigmatic axis.

Meanwhile, the control part 80 is capable of calculating the astigmatic axial angle of the IOL based on positions at the edge of the pupil area 92 at which the astigmatic axis marks 91 have been detected.

Also, the control part 80 calculates a diopter of residual astigmatism based on the angular difference $\Delta\theta$ and combines it with the retro-illumination image (refer to FIG. 5). This diopter of residual astigmatism is a difference between corrected refractive power obtained by correction by the IOL in a case where the IOL is disposed at an appropriate position and actual corrected refractive power. The diopter of residual astigmatism is calculated based on a result of combination of cylindrical refractive power of the cornea and cylindrical refractive power of the IOL. This combination result is derived by the following equation where the spherical dioptic power of the cornea is $S_1$, the cylindrical dioptic power of the cornea is $C_1$, the astigmatic axial angle of the cornea is $A_1$, the spherical dioptic power of the IOL is $S_2$, the cylindrical dioptic power of the IOL is $C_2$, and the astigmatic axial angle of the IOL is $A_2$:

$$C_{12} = -(C_1^2 + C_2^2 + 2C_1 C_2 \cos(2d\theta))^{1/2}$$

Meanwhile, $d\theta$ is an angle representing a misalignment amount of the astigmatic axis of the IOL from a position corresponding to the astigmatic axial angle of the cornea generated by rotation of the astigmatic axis of the IOL centering on the optical axis. That is, $d\theta$ is the above $\Delta\theta$ and is an absolute value of $A_1 - A_2$.

The output data based on the retro-illumination image data depicted in FIG. 5 is utilized when the misalignment amount (axial misalignment amount) between the direction of the astigmatic axis of the TORIC-Intraocular lens and the direction of the astigmatic axis of the examinee's eye is checked after the operation. Such a check is done, for example, in a case where a sufficient correction result cannot be obtained because the IOL has been inserted in the eye in a state where the direction of the astigmatic axis of the examinee's eye and the direction of the astigmatic axis of the IOL are misaligned.

Accordingly, it is possible to check after the operation whether or not the TORIC-Intraocular lens is disposed at an appropriate position in the eye. Thus, it is possible to figure out a cause after the operation when the patient cannot obtain a sufficient correction result.

The retro-illumination image data created by image processing in the above manner is stored on the memory 85. The control part 80 is capable of displaying and outputting the retro-illumination image data on the monitor (output unit) 70, printing the data by a printer (output unit), and transmitting the data to an external device (output unit).

Meanwhile, in the embodiment, the positions of the astigmatic axis marks 91 are detected by use of the retro-illumination image. However, the embodiment is not limited to this configuration, and the control part 80 may detect the positions of the astigmatic axis marks 91, for example, from the anterior segment front image.

Further, in the embodiment, the axial misalignment amount is outputted (displayed) as $\Delta\theta$. However, the embodiment is not limited to this configuration, and angular information for determination of the axial misalignment amount has only to be displayed together with the retro-illumination image. For example, an angular scale (e.g., protractor) for checking the angle between the line M1 and the line B1 may be displayed and combined with the retro-illumination image. In this case, the angular scale may be provided with a position of the line B1 as 0 degrees.

Meanwhile, in the embodiment, the control part 80 displays the line B1 on the retro-illumination image such that the line B1 may pass on the center position between the two detected astigmatic axis marks 91. However, the embodiment is not limited to this configuration, and the control part 80 may display the line B1 and the line M1, for example, by overlapping the end of the line B1 with the end of the line M1. In other words, the line B1 and the line M1 do not need to be overlapped at a specified position. The line B1 and the line M1 may be displayed in any manner as long as the axial misalignment amount between the lines can be checked.

Meanwhile, in the embodiment, axial misalignment information (axial misalignment amount) is displayed on the retro-illumination image. However, the embodiment is not limited to this configuration, and the axial misalignment information may be displayed, for example, on the anterior segment display screen. In this case, the astigmatic axis of the IOL (line M1) on the retro-illumination image may be combined on the anterior segment display screen.

Meanwhile, in the embodiment, in a case where the astigmatic axis marks are formed at a supporting part of the IOL, positions of the astigmatic axis marks formed at the supporting part are detected. The astigmatic axis marks may be any marks as long as they function as marks representing a position or a direction of the astigmatic axis of the lens.

Meanwhile, the axial misalignment amount may be calculated by manual operation. In this case, the control part 80 rotates the line B1 corresponding to the corneal astigmatic axis based on an operation signal from a predetermined switch manually operated by the examiner. Subsequently, the examiner or the control part 80 measures a rotation angle of the line B1 until the astigmatic axis marks 91 and the line B2 are in parallel relationship.

Meanwhile, in the embodiment, in order to detect the positions of the astigmatic axis marks 91, the luminance of the edge of the pupil area 92 is detected on the entire circumference along the circumferential direction of the edge centering on the center O once per degree. However, the embodiment is not limited to this configuration, and luminance change portions corresponding to the astigmatic axis marks 91 may be detected, for example, by scanning the entire display screen in the X or Y direction.

Moreover, the positions of the astigmatic axis marks 91 on the monitor 70 may be designated based on an operation signal from a predetermined switch manually operated by the examiner. In this case, the line B1 may be displayed based on information of the designated positions. In this case, the examiner may use a computer mouse to designate the positions of the astigmatic axis marks 91.

<Ocular Axial Length Measurement>

In the preoperative mode, ocular axial length measurement is performed as well as the kerato imaging and the retro-illumination image imaging. Operations of the present apparatus at the time of ocular axial length measurement are described below. The control part 80 illuminates the measurement light source 1 in a similar manner to that of the aforementioned retro-illumination image imaging. The examinee's eye is irradiated with measurement light by the ocular axial length measuring optical system 10. Reflection light obtained when the measurement light is reflected by the examinee's eye then enters the light receiving device 21 of the light receiving optical system 10b.

The control part 80 causes the first triangular prism 7 to move reciprocatingly by controlling the driving part 71. The control part 80 calculates the ocular axial length based on the timing at which interference light is detected by the light receiving device 21. For example, the control part 80 obtains an interference signal outputted from the light receiving device 21 when the prism 7 is moving. The control part 80 detects by the position detecting sensor 72 a position of the prism 7 when the interference signal is obtained. Subsequently, the control part 80 obtains a value of the ocular axial length based on, for example, the position of the prism 7, a predetermined calculating formula, and a table.

Meanwhile, in the embodiment, the control part 80 obtains the lens astigmatic axis information of the TORIC-Intraocular lens based on the retro-illumination image as one of images in the pupil. However, in the present apparatus, the control part 80 may obtain another image in the pupil by use of the imaging device 35 and obtain the lens astigmatic axis information of the TORIC-Intraocular lens based on this image. In this case, the present apparatus may obtain the image in the pupil by light with which the examinee's eye is irradiated from the front.

Further, in the embodiment, the control part 80 measures the misalignment amount (axial misalignment amount) between the direction of the corneal astigmatic axis and the direction of the intraocular lens astigmatic axis by imaging the examinee's eye in which the TORIC-Intraocular lens has been inserted (TORIC-Intraocular lens insertion eye) in the postoperative mode.

However, the embodiment is not limited to this configuration, and the present apparatus may image the examinee's eye before the TORIC-Intraocular lens is inserted. The operator can reduce the misalignment amount between the direction of the intraocular lens astigmatic axis and the direction of the corneal astigmatic axis by inserting the intraocular lens in the examinee's eye based on the imaged result.

In this case, the control part 80 superimposes a line of the corneal astigmatic axis onto the retro-illumination image, on which an opaque portion (it is approximately in a linear shape in some cases) caused by cataract is displayed. By doing so, the relative positional relationship (axial misalignment amount) between the opaque portion and the corneal astigmatic axis of the examinee's eye is obtained. Based on this positional relationship, the control part 80 or the operator puts a mark at a surface portion (a part of the white of the eye) of the examinee's eye corresponding to the corneal astigmatic axis (when this mark is put, the corneal astigmatic axis is not seen, but the opaque portion is seen). Subsequently, the operator inserts the TORIC-Intraocular lens based on this mark (when the lens is inserted, the corneal astigmatic axis is not seen).

Meanwhile, the optical system of the present apparatus may be provided with a light projecting optical system (e.g., projecting optical system 40) that has a light projecting light source (e.g., ring-shaped light source 41) for projecting measurement light on the cornea of the examinee's eye, an illuminating optical system (e.g., light projecting optical system 10a) for projecting illumination light to image a postoperative retro-illumination image of the examinee's eye in which the TORIC-Intraocular lens has been inserted, and an imaging optical system (e.g., anterior segment front imaging optical system 30) that has an imaging device (e.g., two-dimensional imaging device 35) having an imaging surface disposed at a position to be approximately conjugated with the anterior segment of the examinee's eye for imaging a cornea reflection image by the measurement light and the retro-illumination image of the examinee's eye by the illuminating optical system (e.g., light projecting optical system 10a).

As the light projecting optical system, for example, the projecting optical system 40 for projecting a measurement target to measure the corneal shape is used (e.g., projecting system of a keratometer). The projecting optical system 40 projects, for example, a ring target on the cornea of the examinee's eye. Also, the projecting optical system 40 may have at least three or more point light sources on the concentric circumference centered on the optical axis L1. Further, the light source of the projecting optical system 40 may be an intermittent ring light source. Still further, the projecting optical system 40 may be a placido target projecting optical system for projecting a plurality of ring targets.

As the illuminating optical system (e.g., light projecting optical system 10a), for example, an illuminating optical system for illuminating the fundus of the examinee's eye, or an illuminating optical system for illuminating the anterior segment of the examinee's eye from the front side is used to image the retro-illumination image of the examinee's eye.

Also, the present apparatus is configured to image the retro-illumination image. This facilitates recognition of the positions of the astigmatic axis marks of the TORIC-Intraocular lens. To image the retro-illumination image, for example, the light projecting optical system 10a of the ocular axial length measuring optical system 10 may be used. In this case, the light projecting optical system for the ocular axial length measurement light is also used as an optical system for imaging the retro-illumination image. It is to be understood that a dedicated light projecting optical system may be used to image the retro-illumination image.

Meanwhile, the present disclosure is applicable not only to an optical interference type ocular axial length measurement apparatus but also to an auto refract keratometer. In this case, a measurement light source of the auto refractometer (eye refractive power measuring optical system) may be used to image the retro-illumination image. It is to be understood that the present disclosure is applicable to a mere keratometer.

As the imaging optical system of the present apparatus, for example, the anterior segment front imaging optical system 30 is used. The imaging optical system may be provided with two imaging devices. In this case, an imaging device for measurement of the corneal shape and an imaging device for imaging of the retro-illumination image may be provided.

Further, an optical system (measuring optical system) for measurement of the corneal shape is not limited to a keratometer. As the measuring optical system for measurement of the corneal shape, for example, a light projecting optical system and an imaging optical system for imaging an anterior segment cross-sectional image based on OCT or the Scheimpflug principle may be used.

Moreover, to detect the axial misalignment amount, the control part 80 may detect the angle of the astigmatic axis marks with respect to the direction of the corneal astigmatic axis with reference to a certain center point by image processing.

Also, the ophthalmic apparatus of the embodiment can be expressed as the following first ophthalmic apparatus. That is, the first ophthalmic apparatus includes a light projecting optical system for projecting measurement light on a cornea of an examinee's eye, a first imaging optical system for imaging a cornea reflection image obtained by reflection of the measurement light at the cornea, a measuring optical system for measuring a corneal shape of the examinee's eye, a computing unit for measuring a direction of a corneal astigmatic axis based on the cornea reflection image, an illuminating optical system for projecting illumination light toward a fundus of the examinee's eye, a second imaging optical system for imaging a retro-illumination image in a pupil of the examinee's eye obtained by reflection of the illumination light at the fundus, an image processing unit for combining a first target representing the direction of the astigmatic axis based on the measurement result at the computing unit with the retro-illumination image imaged by the second imaging optical system, and an output unit for outputting the retro-illumination image combined by the image processing unit. In this first ophthalmic apparatus, the measuring optical system may be either a keratometer optical system or an anterior segment cross-sectional image imaging optical system.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An ophthalmic apparatus, comprising:
    a light projecting optical system for projecting measurement light on a cornea of an examinee's eye;
    a first imaging optical system for imaging a cornea reflection image from reflection of the measurement light at the cornea;
    a computing unit for obtaining a direction of a corneal astigmatic axis based on the cornea reflection image;
    an illuminating optical system for projecting illumination light towards a fundus of the examinee's eye;
    a second imaging optical system for imaging a retro-illumination image in a pupil of the examinee's eye from reflection of the illumination light at the fundus; and
    an image processing unit for superimposing a first target representing the direction of the corneal astigmatic axis obtained by the computing unit based on the cornea reflection mage on the retro-illumination image.

2. The ophthalmic apparatus according to claim 1, further comprising a TORIC-Intraocular lens inserted in the examinee's eye, wherein
    the computing unit is adapted to obtain a direction of an astigmatic axis of the TORIC-Intraocular lens based on the retro-illumination image, and
    the image processing unit is adapted to further superimpose a second target representing the direction of the astigmatic axis of the TORIC-Intraocular lens on the retro-illumination image together with the first target.

3. The ophthalmic apparatus according to claim 2, wherein
    the TORIC-Intraocular lens includes an astigmatic axis mark formed thereon, and
    the computing unit is adapted to measure the direction of the astigmatic axis of the TORIC-Intraocular lens by detecting the astigmatic axis mark based on the retro-illumination image.

4. The Ophthalmic apparatus according to claim 3, wherein the computing unit is further adapted to obtain an axial misalignment amount that is a misalignment amount between the direction of the corneal astigmatic axis and the direction of the astigmatic axis of the TORIC-Intraocular lens.

5. The Ophthalmic apparatus according to claim 1, wherein the computing unit is further adapted to obtain an optical center position of the TORIC-Intraocular lens by processing the retro-illumination image, to obtain a corneal center position of the examinee's eye based on the cornea reflection image, and to detect a misalignment amount between the corneal center position and the optical center position.

6. The Ophthalmic apparatus according to claim 1, further comprising:
   an ocular axial length measuring optical system for projecting measurement light on the examinee's eye and detecting interference light formed from reflection light from the examinee's eye, wherein
   the illuminating optical system is adapted to project the measurement light of the ocular axial length measuring optical system.

7. The Ophthalmic apparatus according to claim 1, wherein the light projecting optical system and the first imaging optical system constitute a keratometer optical system or an anterior segment cross-sectional image imaging optical system.

8. A method of obtaining a retro-illumination image of an examinee's eye by use of the ophthalmic apparatus according to claim 1, the method comprising:
   obtaining the direction of the corneal astigmatic axis of the examinee's eye before an operation using an intraocular lens and the retro-illumination image;
   superimposing the first target on the retro-illumination image; and
   obtaining the retro-illumination image on which the first target is superimposed.

9. A method of obtaining a retro-illumination image of a examinee's eye by use of the ophthalmic apparatus according to claim 1, the method comprising:
   obtaining the direction of the corneal astigmatic axis of the examinee's eye after an operation using an intraocular lens and the retro-illumination image;
   superimposing the first target on the retro-illumination image; and
   obtaining the retro-illumination image on which the first target is superimposed.

10. The ophthalmic apparatus according to claim 1, further comprising an output unit for outputting the retro-illumination image on which the first target is superimposed.

11. The ophthalmic apparatus according to claim 4, further comprising an output unit for outputting the axial misalignment amount together with the retro-illumination image.

12. The ophthalmic apparatus according to claim 5, further comprising an output unit for outputting the misalignment amount together with the retro-illumination image.

* * * * *